(12) United States Patent
Wei (10) Patent No.: US 12,208,383 B2
(45) Date of Patent: Jan. 28, 2025

(54) BIOCHEMICAL DETECTION DEVICE

(71) Applicant: Han Hung, Taichung (TW)

(72) Inventor: Chih-Ping Wei, Tainan (TW)

(73) Assignee: Han Hung, Taichung (TW)

( * ) Notice: Subject to any disclaimer, the term of this patent is extended or adjusted under 35 U.S.C. 154(b) by 806 days.

(21) Appl. No.: 17/443,549

(22) Filed: Jul. 27, 2021

(65) Prior Publication Data
US 2023/0037035 A1    Feb. 2, 2023

(51) Int. Cl.
*B01L 3/00*    (2006.01)
*G01N 33/569*    (2006.01)

(52) U.S. Cl.
CPC .......... *B01L 3/50* (2013.01); *G01N 33/56983* (2013.01); *B01L 2200/0689* (2013.01); *B01L 2200/082* (2013.01); *B01L 2300/042* (2013.01); *B01L 2300/0832* (2013.01); *B01L 2300/126* (2013.01)

(58) Field of Classification Search
CPC ............... B01L 3/50; B01L 2200/0689; B01L 2200/082; B01L 2300/042; B01L 2300/0832; B01L 2300/126; G01N 33/56983
See application file for complete search history.

(56) References Cited

U.S. PATENT DOCUMENTS

| | | | | |
|---|---|---|---|---|
| 3,838,785 | A * | 10/1974 | Lancesseur | B65D 41/60 215/277 |
| 8,394,627 | B2 * | 3/2013 | Fitzgerald | G01N 33/72 435/288.1 |
| 2009/0024055 | A1 * | 1/2009 | Nguyen | A61B 10/0096 435/7.1 |
| 2020/0384458 | A1 * | 12/2020 | Nguyen | B01L 3/502 |

FOREIGN PATENT DOCUMENTS

CN    102325501 A  *  1/2012    ......... A61B 10/0038

* cited by examiner

*Primary Examiner* — Jill A Warden
*Assistant Examiner* — Michael Stanley Gzybowski
(74) *Attorney, Agent, or Firm* — Chun-Ming Shih; HDLS IPR SERVICES (57) ABSTRACT

A biochemical detection device is revealed. The biochemical detection device includes a cap and a base arranged at two ends of a test tube correspondingly and a driving member disposed on the base. A sample-mounting slot and a test-paper-mounting slot separated from each other are formed in the test tube. After sampling, a sample obtained is placed into the sample-mounting slot and mixed with an extraction solution therein. A thin-film on the sample-mounting slot is penetrated by the driving member to allow the extraction solution mixed with the sample flowing into a cavity of the test tube to react with a test strip in the test-paper-mounting slot. The test cost is reduced and the detection efficiency is improved due to simple structure and easy operation. Moreover, the sample and the extraction solution are sealed in the test tube to prevent environmental pollution caused by spread of viruses.

9 Claims, 8 Drawing Sheets

BIOCHEMICAL DETECTION DEVICE

BACKGROUND OF THE INVENTION

Field of the Invention

The present invention relates to a detection device, especially to a biochemical detection device which not only features on simple structure, easy operation, lower test cost and better detection efficiency but also prevents environmental pollution caused by leakage of samples and extraction solutions.

Description of Related Art

Generally, a test kit for rapid screening available now mainly includes a swab, a test tube, a nozzle cap, and a test cassette. The cost is high due to multiple components and the operation process is complicated. During the operation, users need to note that whether the test cassette is placed on a flat surface and the amount of a mixture of extraction buffer and the sample being added. Even a little bit of human error will affect the accuracy of test results and the user needs to take the test again so that the detection efficiency is lowered. The mixture of extraction buffer and the sample may be splashed or dropped onto other areas during the operation process, which could cause the spread of viruses. After completing the test, users need to place the swab, the test tube, the nozzle cap, and the test cassette into a plastic bag in order to prevent environmental pollution. The test kit is inconvenient to use so that there is room for improvement and there is a need to provide a novel detection device.

SUMMARY OF THE INVENTION

Therefore, it is a primary object of the present invention to provide a biochemical detection device which not only features on simple structure, easy operation, reduced test cost and higher detection efficiency but also protects environment from pollution caused by leakage of samples and extraction solutions.

In order to achieve the above object, a biochemical detection device according to the present invention mainly includes a cap and a base arranged at two ends of a test tube correspondingly and a driving member disposed on the base. A sample-mounting slot and a test-paper-mounting slot are formed in the test tube and separated from each other. After sampling, a sample is placed into the sample-mounting slot to be stirred and mixed with an extraction solution therein. Then a thin-film on one end of the sample-mounting slot is penetrated by the driving member to allow the extraction solution mixed with the sample flowing into a cavity of the test tube and in contact with a test strip in the test-paper-mounting slot to have reaction. Owing to the simple structure and easy operation, the test cost is reduced and the detection efficiency is improved effectively. Moreover, the sample and the extraction solution are both sealed in the test tube so as to prevent environmental pollution caused by the spread of viruses.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
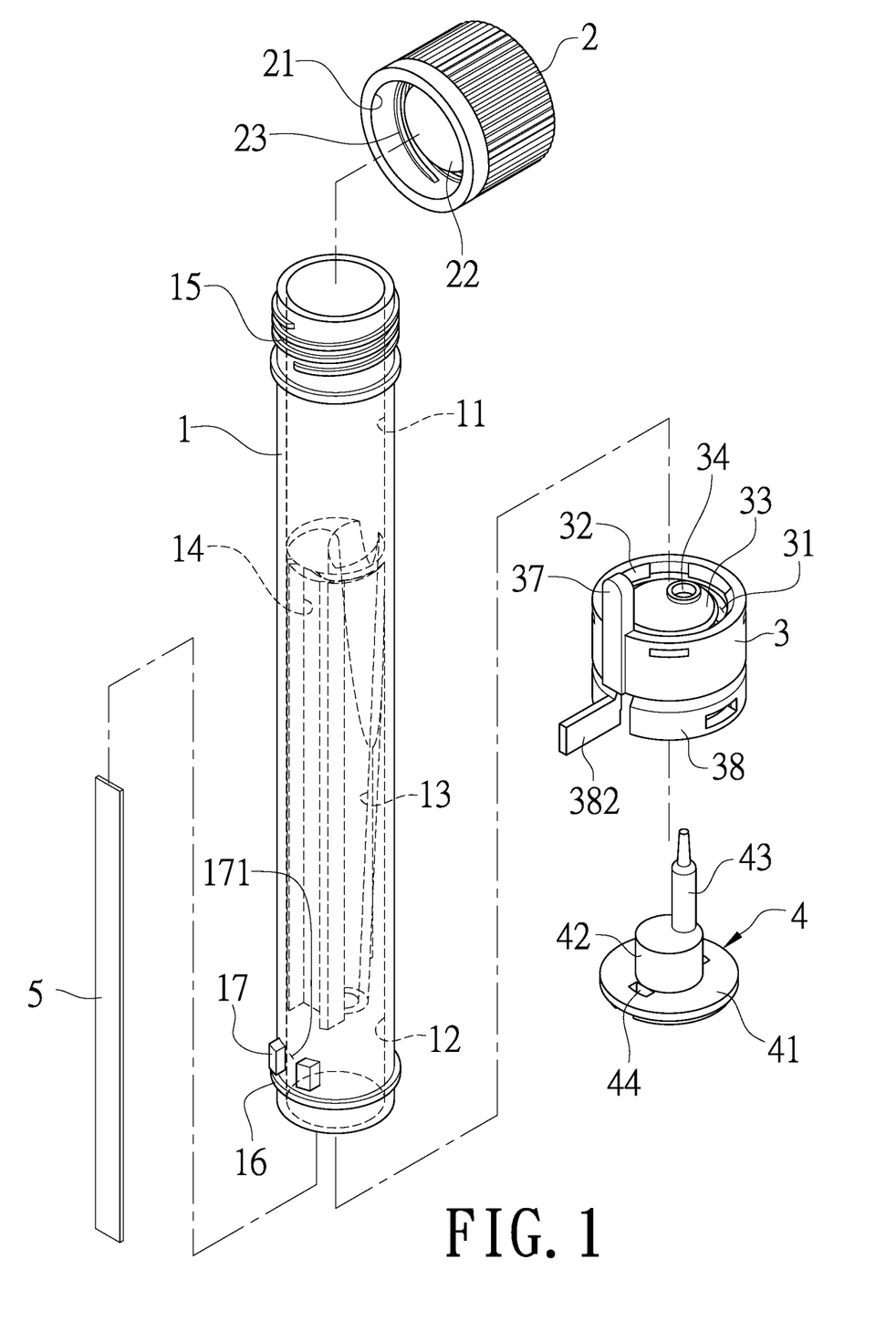
FIG. 1 is an exploded view of an embodiment according to the present invention.
Figure 2:
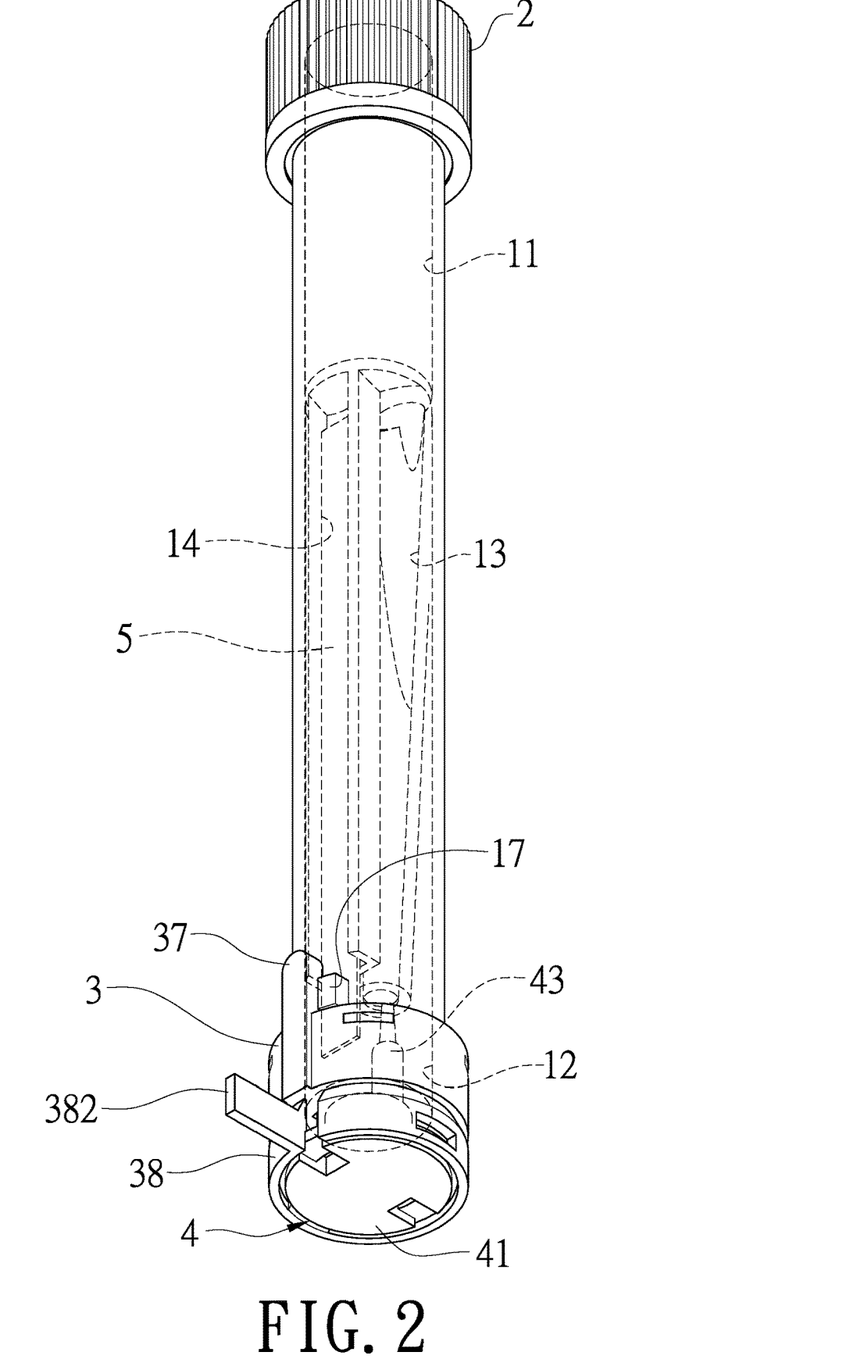
FIG. 2 is a perspective view of an embodiment according to the present invention.
Figure 3:
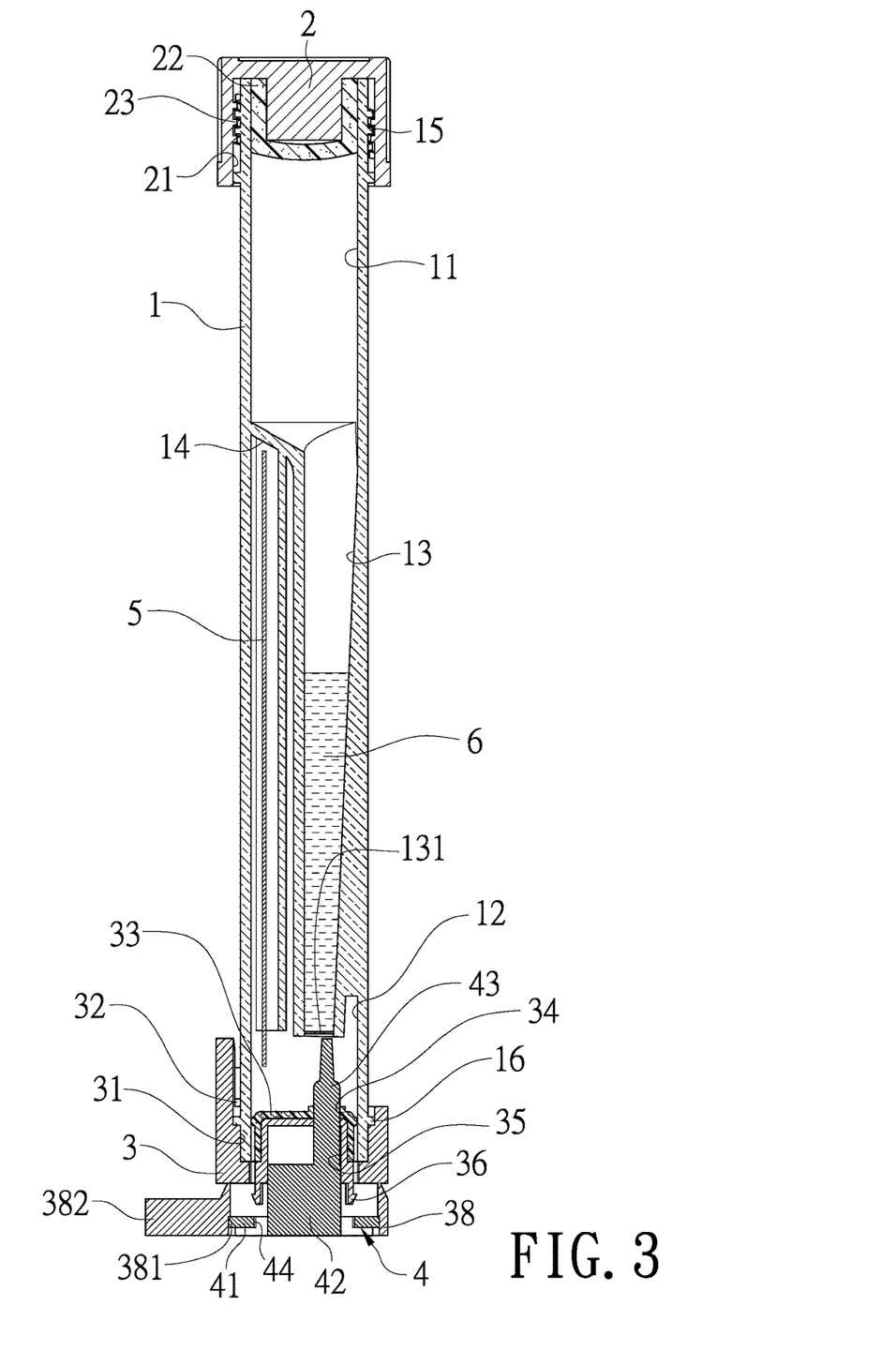
FIG. 3 is a sectional view of an embodiment according to the present invention.

Refer to FIG. 1, FIG. 2 and FIG. 3, a biochemical detection device according to the present invention mainly includes a test tube 1, a cap 2 and a base 3 arranged at an upper end and a lower end of the test tube 1 respectively, and a driving member 4.

The test tube 1 consists of a first cavity 11, a second cavity 12, a sample-mounting slot 13, a test-paper-mounting slot 14, an outer threaded portion 15, a first mounting portion 16, and two positioning blocks 17. The first cavity 11 and the second cavity 12 are disposed on an upper end and a lower end of the test tube 1 respectively while the sample-mounting slot 13 and the test-paper-mounting slot 14 are located between the first and the second cavities 11, 12 and separated from each other. An upper end and a lower end of the sample-mounting slot 13 are communicated with the first cavity 11 and the second cavity 12 respectively. The sample-mounting slot 13 which tapers from the upper end to the lower end thereof is provided with a thin-film 131 covering the lower end thereof. An opening of the test-paper-mounting slot 14 faces the second cavity 12 so that the test-paper-mounting slot 14 is communicated with the second cavity 12. The outer threaded portion 15 and the first mounting portion 16 are formed on an outer wall of the upper end and the outer wall of the lower end of the test tube 1 respectively. As to the two positioning blocks 17, they are formed over the first mounting portion 16 on an outer wall of the test tube 1 and a positioning concave portion 171 is formed between the positioning blocks 17.

The cap 2 is composed of a cover chamber 21 covering the upper end of the test tube 1 correspondingly, a first plug 22 formed in the cover chamber 21 for being plugged into the first cavity 11 on the upper end of the test tube 1, and an inner threaded portion 23 formed on an inner wall of the cover chamber 21 and capable of being engaged with the outer threaded portion 15 on the outer wall of the upper end of the test tube 1 correspondingly.

The base 3 includes a mounting slot 31 disposed concavely on an upper end thereof for mounting the lower end of the test tube 1 correspondingly, at least one second mounting portion 32 which is formed on a wall surface of the mounting slot 31 and capable of being engaged with the first mounting portion 16 on the outer wall of the lower end of the test tube 1, a second plug 33 formed on the bottom of the mounting slot 31 thereof for being plugged into the second cavity 12 on the lower end of the test tube 1, a through hole 34 arranged at the second plug 33 and corresponding to the lower end of the sample-mounting slot 13 of the test tube 1, a concave portion 35 formed on a lower end thereof at the position opposite to the second plug 33 and communicated with the through hole 34, and at least one first locking portion 36 which is a tenon formed on the lower end thereof. In a preferred embodiment, each of two sides of the concave portion 35 is provided with the first locking portion 36. Moreover, a positioning bar 37 is formed on an outer surface of the base 3 for being mounted and positioned in the positioning concave portion 171 on the outer wall of the test tube 1. The base 3 further includes a safety ring 38 which is disposed around the lower end of the base 3 and connected and disconnected with the lower end of the base 3 by a point. At least one stopping flange 381 is formed on an inner surface of the safety ring 38 while a drawing portion 382 is projecting from an outer surface of the safety ring 38.

The driving member 4 which is arranged at the lower end of the base 3 is provided with a bottom disc 41, a protruding block 42, a piercing pin 43, and at least one second locking portion 44 disposed on the bottom disc 41. The bottom disc 41 and the stopping flange 381 of the safety ring 38 on the lower end of the base 3 are abutting against each other for positioning. The protruding block 42 is located at the center of the bottom disc 41 and mounted into the concave portion 35 of the base 3 correspondingly. The piercing pin 43 is formed on the protruding block 42 and inserted into the through hole 34 of the base 3 correspondingly. The second locking portion 44 is a locking hole. In a preferred embodiment, each of two opposite sides of the protruding block 42 is provided with one second locking portion 44 which is engaged and locked with the first locking portion 36 on the lower end of the base 3 correspondingly.

A test strip 5 is placed into the test-paper-mounting slot 14 of the test tube 1 and having one end thereof extending to the second cavity 12 of the test tube 1.

An extraction solution 6 is filled into the sample-mounting slot 13 of the test tube 1.

Figure 4:
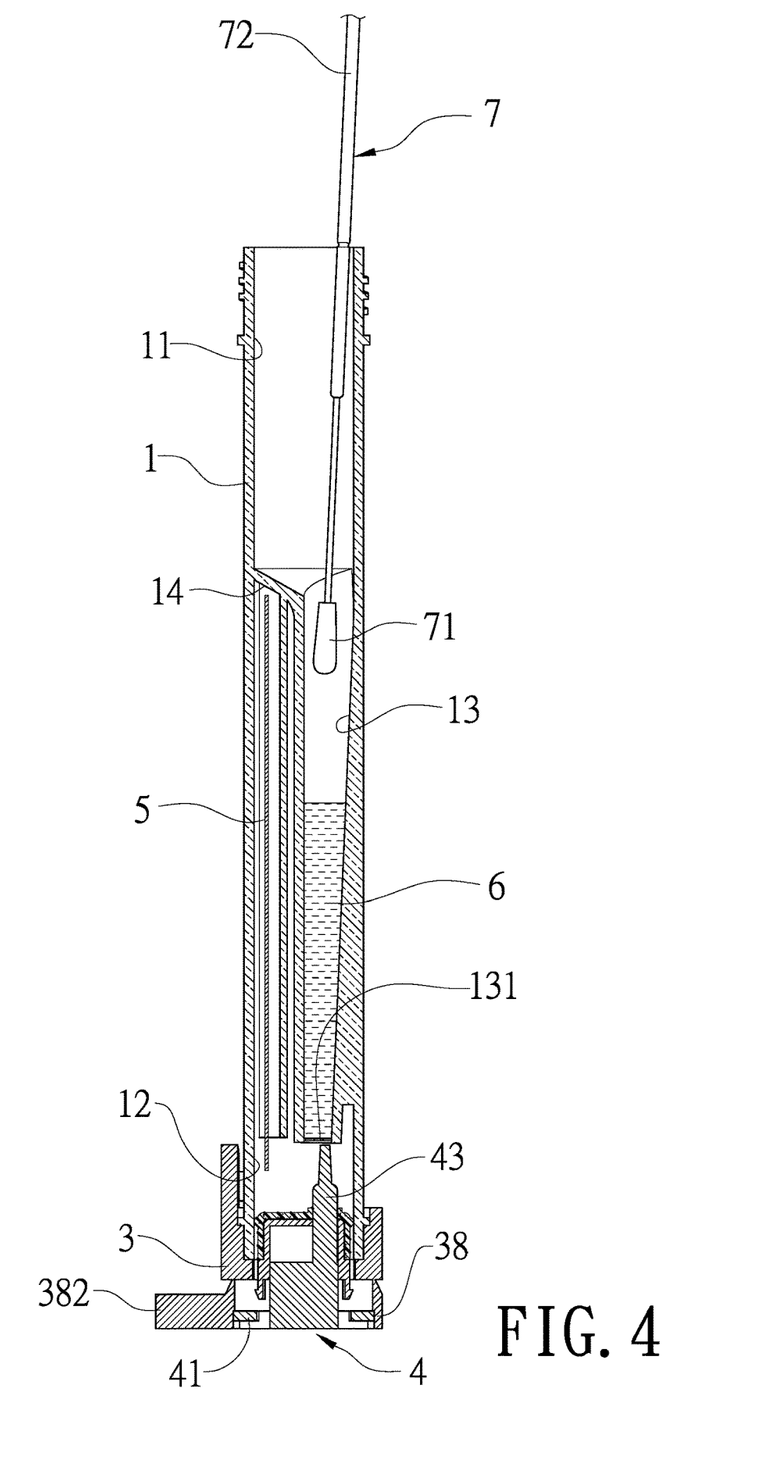
FIG. 4 is a first sectional view of an embodiment in use according to the present invention.
Figure 5:
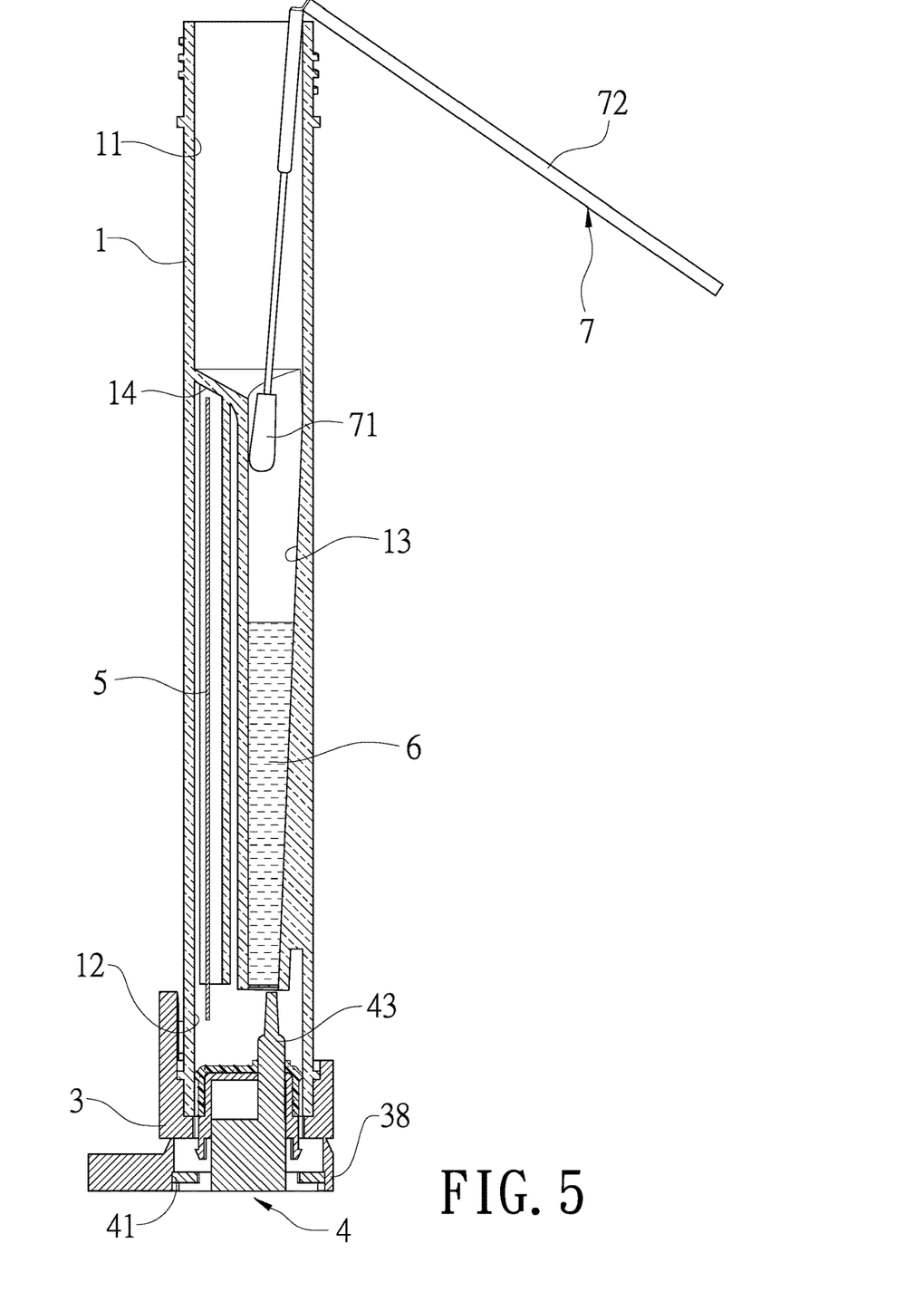
FIG. 5 is another sectional view of an embodiment in use according to the present invention.
Figure 6:
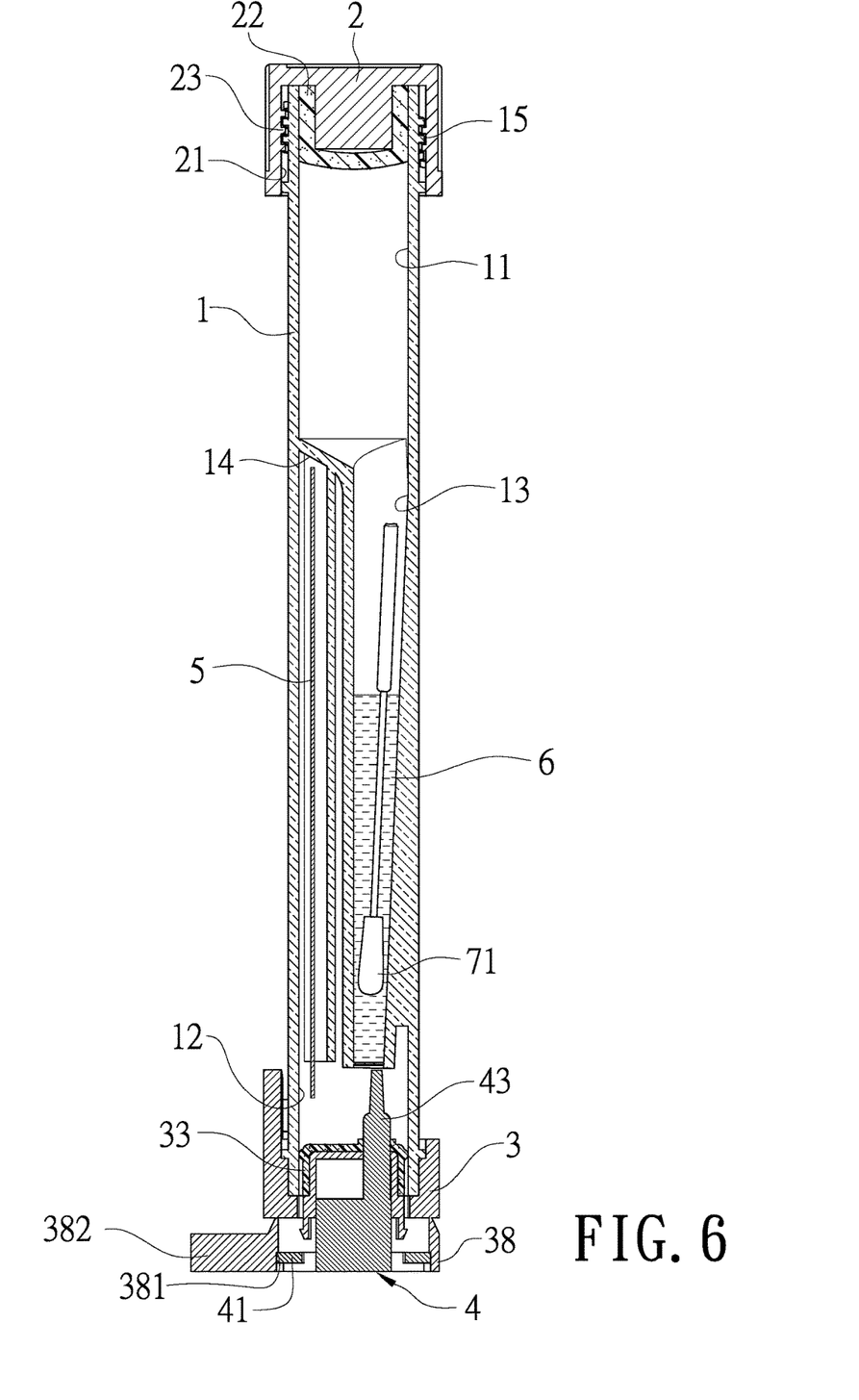
FIG. 6 is a further sectional view of an embodiment in use according to the present invention.

While performing virus detection such as coronavirus, as shown in FIG. 4, a swab 7 with a sample attached thereof is moved through the first cavity 11 on the upper end of the test tube 1 and then a sampling portion 71 of the swab 7 is inserted into the sample-mounting slot 13 to be stirred in the extraction solution 6 filled in the sample-mounting slot 13 in advance. Then also refer to FIG. 5, a handheld portion 72 of the swab 7 is broken off by a user and only the sampling portion 71 is left in the test tube 1. Also refer to FIG. 6, next the cap 2 is placed and fixed on the upper end of the test tube 1 by the inner threaded portion 23 of the cap 2 and the outer threaded portion 15 of the test tube 1 threaded and engaged with each other and the first plug 22 of the cap 2 plugged and mounted into the first cavity 11 of the test tube 1. Thereby the extraction solution 6 already mixed with the sample will not leak out.

Figure 7:
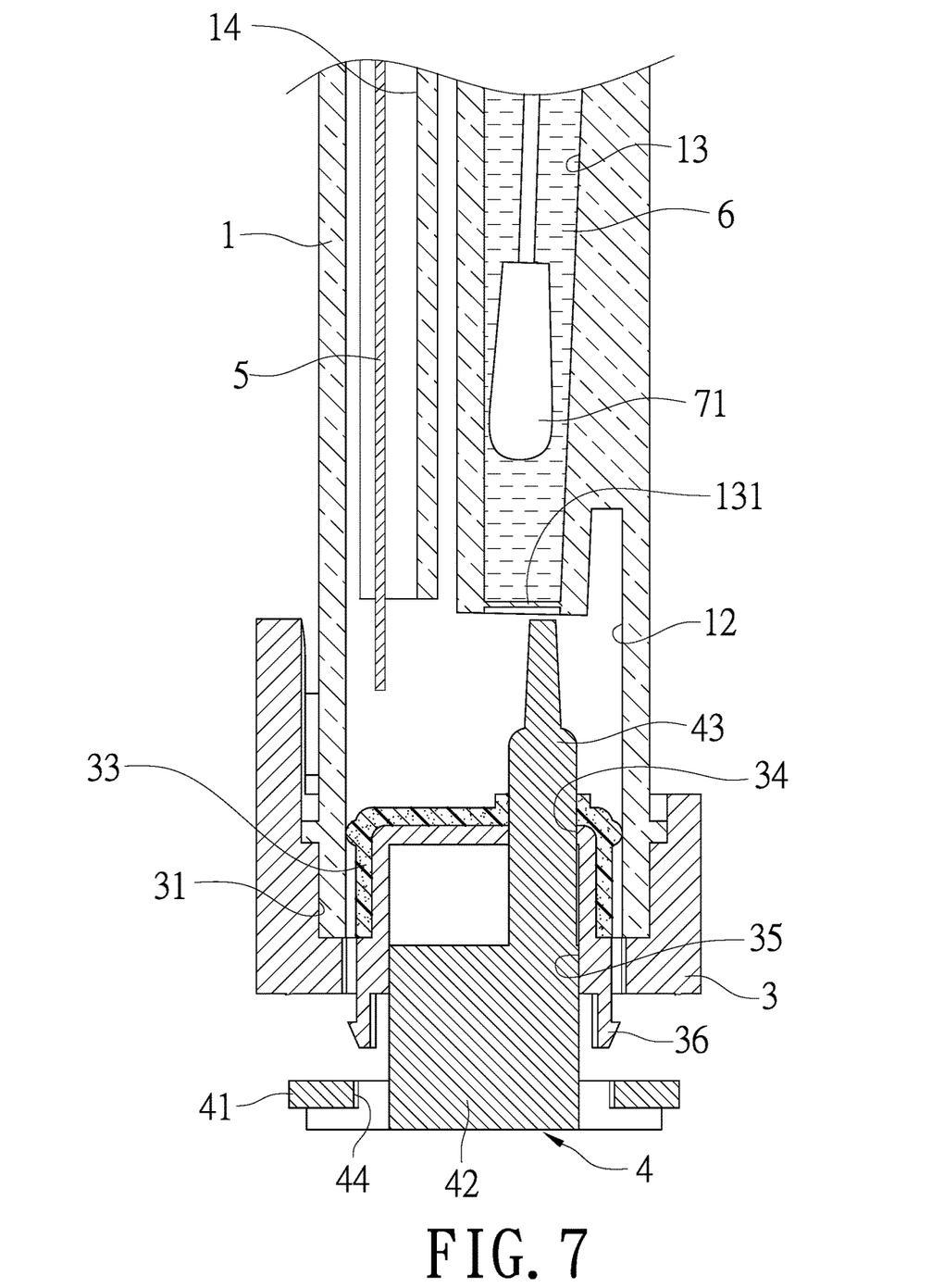
FIG. 7 is a further sectional view of an embodiment in use according to the present invention.
Figure 8:
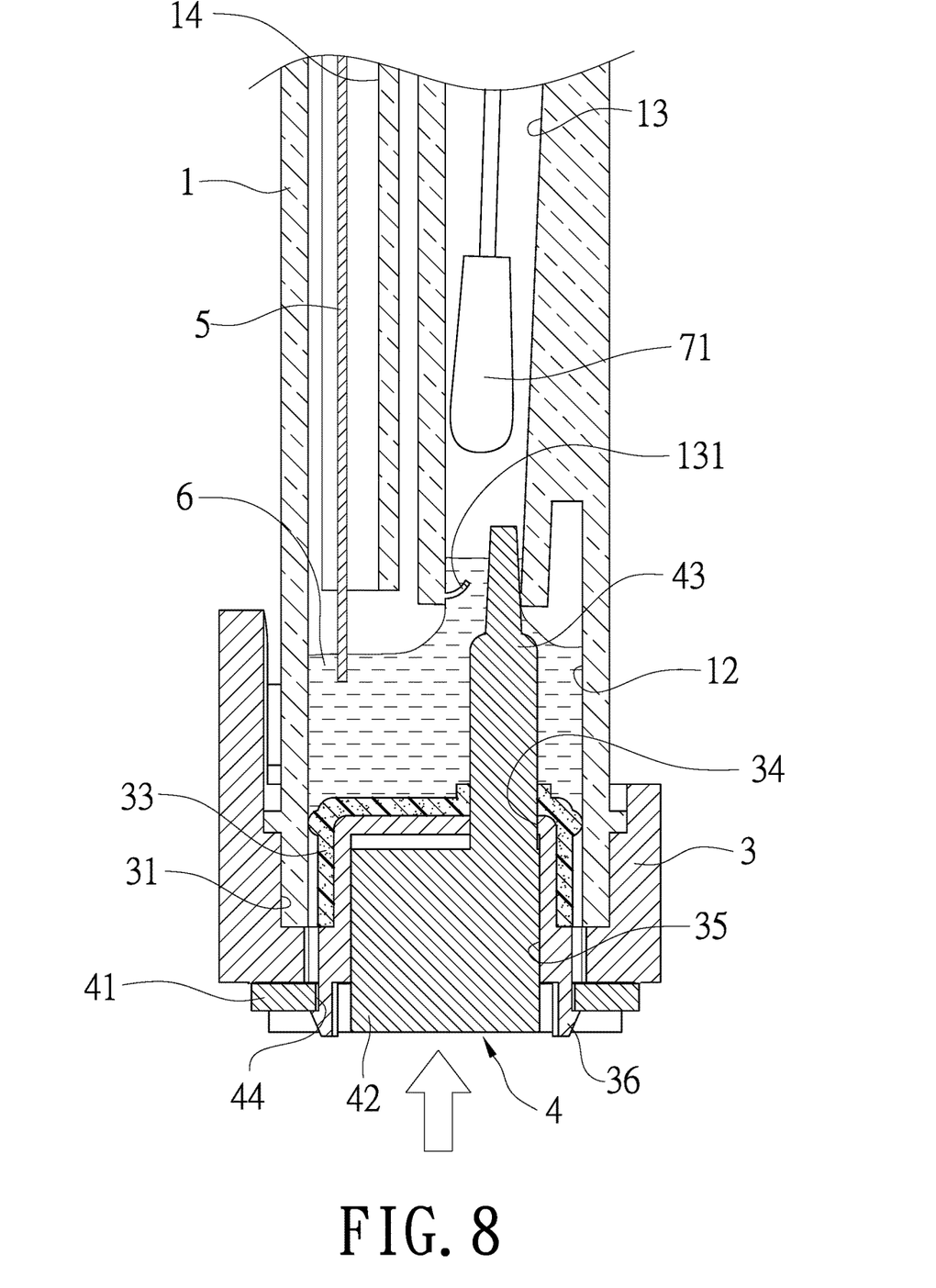
FIG. 8 is a further sectional view of an embodiment in use according to the present invention.

After waiting for one minute to allow the sample and the extraction solution 6 mixed well with each other, as shown in FIG. 7, the user can manually hold the drawing portion 382 of the safety ring 38 of the base 3 to separate the drawing portion 382 from the base 3 so that the bottom disc 41 of the driving member 4 and the stopping flange 381 on the inner surface of the safety ring 38 are released, without being positioned by each other. Refer to FIG. 8, then the user can push the driving member 4 upward so that the piercing pin 43 of the driving member 4 is penetrating the thin-film 131 on the lower end of the sample-mounting slot 13. While the driving member 4 is moved upward, the second locking portion 44 on the bottom disc 41 of the driving member 4 is engaged with the first locking portion 36 on the lower end of the base 3 correspondingly for maintaining the piercing pin 43 at the state of being inserted into the sample-mounting slot 13.

After the piercing pin 43 inserted into the sample-mounting slot 13, both the sample-mounting slot 13 and the test-paper-mounting slot 14 are communicated with the second cavity 12 of the test tube 1. At the moment, the extraction solution 6 mixed with the sample in the sample-mounting slot 13 is flowing into the second cavity 12 of the test tube 1 to contact with the test strip 5 in the test-paper-mounting slot 14. After the test strip 5 being soaked thoroughly to have reaction and changes, users can observe the changes of the test strip 5 through the test tube 1 and learn the test result.

In the present invention, the sampling portion 71 of the swab 7, the sample, and the extraction solution 6 mixed with the sample are all mounted and sealed in the close test tube 1 during the test process. The user doesn't need to take time for cleaning up after completing the test so that the present biochemical detection device is more convenient to use. Moreover, the present device has simple structure, fewer components, and low cost so that detection cost is reduced. The operation procedure is simple and easy so that human errors which affect accuracy of test results are minimized to avoid retests and increase detection efficiency. In addition, the sampling portion 71, the sample, and the extraction solution 6 mixed with the sample are all sealed in the close test tube 1 during and after the test. Thereby the pollution of the environment caused by the spread of the virus can be avoided and the safety in use is improved.

Besides detection of coronavirus, the present device can also be applied to tests for detecting pathogens such as influenza virus and bacteria, biological tissues, body fluids, chemical substances, etc.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalent.

What is claimed is:

1. A biochemical detection device comprising:
a test tube which includes a first cavity and a second cavity disposed on an upper end and a lower end thereof respectively, and a sample-mounting slot and a test-paper-mounting slot located between the first cavity and the second cavity and separated from each other; an upper end and a lower end of the sample-mounting slot are in communication with the first cavity and the second cavity respectively; the sample-mounting slot is provided with a thin-film covering the lower end thereof and an opening of the test-paper-mounting slot faces the second cavity so that the test-paper-mounting slot is in communication with the second cavity;
a cap provided with a cover chamber which covers the upper end of the test tube;
a base which includes a mounting slot disposed concavely on an upper end of the base for mounting the base to the lower end of the test tube, a through hole arranged at a bottom of the mounting slot and in communication with said second cavity, and a safety ring which is disposed around a lower end of the base to be connected and disconnected with the lower end of the base by a plurality of breakable points and having at least one stopping flange formed on an inner surface of the safety ring and a drawing portion projecting from an outer surface of the safety ring; and a second plug is formed on the bottom of the mounting slot of the base for being plugged into the second cavity on the lower end of the test tube, the through hole being in vertical alignment with the sample mounting slot;

a driving member which is arranged at the lower end of the base and provided with a bottom disc abutting against the at least one stopping flange of the safety ring on the lower end of the base for positioning the driving member against the at least one stopping flange of the safety ring on the base, and a piercing pin formed on the bottom disc and inserted into the through hole of the base.

2. The biochemical detection device as claimed in claim 1, wherein a test strip is mounted into the test-paper-mounting slot of the test tube.

3. The biochemical detection device as claimed in claim 1, wherein an extraction solution is filled into the sample-mounting slot of the test tube.

4. The biochemical detection device as claimed in claim 1, wherein the sample-mounting slot tapers from the upper end to the lower end thereof.

5. The biochemical detection device as claimed in claim 1, wherein a first plug is formed in the cover chamber of the cap for being plugged into the first cavity on the upper end of the test tube.

6. The biochemical detection device as claimed in claim 1, wherein a first mounting portion is formed on an outer wall of the lower end of the test tube and at least one second mounting portion is arranged at a wall surface of the mounting slot of the base for being engaged with the first mounting portion on the lower end of the test tube.

7. The biochemical detection device as claimed in claim 1, wherein a concave portion is arranged at the lower end of the base, located opposite to the second plug, and is in communication with the through hole; a protruding block is located at the center of the bottom disc of the driving member and mounted into the concave portion and the piercing pin being formed on the protruding block.

8. A biochemical detection device comprising:

a test tube which includes a first cavity and a second cavity disposed on an upper end and a lower end thereof respectively, and a sample-mounting slot and a test-paper-mounting slot located between the first cavity and the second cavity and separated from each other; an upper end and a lower end of the sample-mounting slot are in communication with the first cavity and the second cavity respectively; the sample-mounting slot is provided with a thin-film covering the lower end thereof and an opening of the test-paper-mounting slot faces the second cavity so that the test-paper-mounting slot is in communication with the second cavity;

a cap provided with a cover chamber which covers the upper end of the test tube;

a base which includes a mounting slot disposed concavely on an upper end of the base for mounting the base to the lower end of the test tube, a through hole arranged at a bottom of the mounting slot and in communication with said second cavity, and a safety ring which is disposed around a lower end of the base to be connected and disconnected with the lower end of the base by a plurality of breakable points and having at least one stopping flange formed on an inner surface of the safety ring and a drawing portion projecting from an outer surface of the safety ring; and a driving member which is arranged at the lower end of the base and provided with a bottom disc abutting against the at least one stopping flange of the safety ring on the lower end of the base for positioning the driving member against the at least one stopping flange of the safety ring on the base, and a piercing pin formed on the bottom disc and inserted into the through hole of the base, wherein at least one first locking portion is formed on the lower end of the base and at least one second locking portion is disposed on the bottom disc of the driving member for being locked with the first locking portion on the lower end of the base.

9. A biochemical detection device comprising:

a test tube which includes a first cavity and a second cavity disposed on an upper end and a lower end thereof respectively, and a sample-mounting slot and a test-paper-mounting slot located between the first cavity and the second cavity and separated from each other; an upper end and a lower end of the sample-mounting slot are in communication with the first cavity and the second cavity respectively; the sample-mounting slot is provided with a thin-film covering the lower end thereof and an opening of the test-paper-mounting slot faces the second cavity so that the test-paper-mounting slot is in communication with the second cavity;

a cap provided with a cover chamber which covers the upper end of the test tube;

a base which includes a mounting slot disposed concavely on an upper end of the base for mounting to the base to the lower end of the test tube, a through hole arranged at a bottom of the mounting slot and in communication with said second cavity, and a safety ring which is disposed around a lower end of the base to be connected and disconnected with the lower end of the base by a plurality of breakable points and having at least one stopping flange formed on an inner surface of the safety ring and a drawing portion projecting from an outer surface of the safety ring;

a driving member which is arranged at the lower end of the base and provided with a bottom disc abutting against the at least one stopping flange of the safety ring on the lower end of the base for positioning the driving member against the at least one stopping flange of the safety ring on the base, and a piercing pin formed on the bottom disc and inserted into the through hole of the base, wherein two positioning blocks are formed on an outer wall of the lower end of the test tube and a positioning concave portion is formed between the two positioning blocks, a positioning bar is mounted on an outer surface of the base for being mounted and positioned in the positioning concave portion on the outer wall of the test tube.

* * * * *